United States Patent [19]

Malabarba et al.

[11] Patent Number: 5,164,484
[45] Date of Patent: Nov. 17, 1992

[54] DE-(ACETYLGLUCOSAMINYL-DI(DEHYDRO)-DEOXY TEICOPLANIN DERIVATIVES

[75] Inventors: Adriano Malabarba, Binasco; Pietro Ferrari, Ferriere; Aldo Trani, Milan; Giorgio Tarzia, Saronno, all of Italy

[73] Assignee: Gruppo Lepetit S.p.A., Milan, Italy

[21] Appl. No.: 778,764

[22] Filed: Oct. 21, 1991

Related U.S. Application Data

[60] Continuation of Ser. No. 590,322, Sep. 28, 1990, abandoned, which is a continuation of Ser. No. 243,388, Sep. 12, 1988, abandoned, which is a division of Ser. No. 102,198, Jul. 17, 1987, Pat. No. 4,789,661.

[30] Foreign Application Priority Data

Nov. 28, 1985 [GB] United Kingdom ................ 8529272

[51] Int. Cl.$^5$ ................................................ C07K 1/00
[52] U.S. Cl. .................................... 530/345; 530/317; 530/322; 930/190; 930/270; 930/DIG. 510

[58] Field of Search ................. 530/317, 322, 345

[56] References Cited

U.S. PATENT DOCUMENTS

4,239,751  12/1980  Coronelli et al. ............... 424/118
4,604,239  8/1986   Michel et al. .................... 530/317

OTHER PUBLICATIONS

Barna et al., The Journal of Antibiotics, vol. 37, No. 10, pp. 1204–1208 (Oct. 1984).

*Primary Examiner*—Y. Christina Chan
*Attorney, Agent, or Firm*—Michael J. Sayles

[57] ABSTRACT

The present invention is directed to new de-(acetylglucosaminyl)-di(dehydro)deoxy teicoplanin derivatives which possess antibiotic activity mainly against gram positive bacteria.

The new compounds are obtained by chemical modification of a teicoplanin antibiotic substance.

11 Claims, No Drawings

DE-(ACETYLGLUCOSAMINYL-DI(DEHYDRO)-DEOXY TEICOPLANIN DERIVATIVES

This a continuation of application Ser. No. 590,322, filed Sep. 28, 1990, now abandoned which is a continuation of application Ser. No. 243,388, filed Sep. 12, 1988, now abandoned, which is a divisional of application Ser. No. 102,198, filed Jul. 17, 1987, issued Dec. 6, 1988 as a U.S. Pat. No. 4,789,661.

The present invention is directed to new antibiotic substances which are de-(acetylglucosaminyl)-di(dehydro)deoxy teicoplanin derivatives of the following formula I

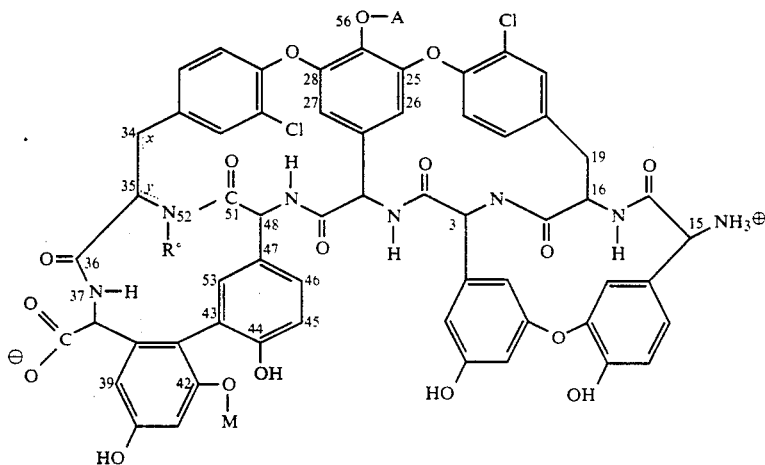

wherein
- x and y each independently represents nil or an additional bond, A represents hydrogen or N-[($C_{10}$–$C_{11}$)aliphatic acyl]-$\beta$-D-2-deoxy-2-aminoglucopyranosyl, M represents hydrogen or $\alpha$-D-mannopyranosyl, $R^o$ represents nil when y represents an additional bond and hydrogen when y represents nil, with the proviso that when x represent an additional bond y must represent nil, and when x represent nil y must represent an additional bond and when M represents hydrogen also A must represent hydrogen, and the addition salts thereof.

In the present disclosure and claims ($C_{10}$–$C_{11}$)aliphatic acyl represent a saturated or unsaturated aliphatic acyl group of 10 or 11 carbon atoms. Preferred examples of ($C_{10}$–$C_{1}$)aliphatic acyl groups are: Z-4-decenoyl, 8-methylnonanoyl, decanoyl, 8-methyldecanoyl, and 9-methyldecanoyl.

When A and M represent sugar moieties as above defined, they are linked to the core moiety through O-glycosidic bonds.

A preferred group of compounds of the invention includes those compounds of formula I wherein x represents nil and y represents an additional bond. Another preferred group of compounds of the invention is represented by those compounds of formula I wherein the amidic bond 36,37 has a trans configuration. The most preferred group of compounds of the invention is represented by those compounds of formula I wherein x represents nil, y represents an additional bond and the amidic bond 36,37 has a trans configuration The compounds of the invention possess antimicrobial activity, mainly against gram positive bacteria, some coagulase-negative staphylococci included. They are prepared by reacting teicoplanin, a teicoplanin factor, component or pseudoaglycon under controlled base conditions in the presence of polar organic solvents.

Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures.

Teichomycin $A_2$, which is the major factor of the isolated antibiotic complex, is then separated from the other factors by means of column chromatography on SEPHADEX ®.

British Patent Application Publication No. 2121401 discloses that antibiotic Teichomycin A2 actually is a mixture of five closely related co-produced main components.

According to recent structural studies it is possible to represent teicoplanin $A_2$ (formerly Teichomycin $A_2$) main components 1, 2, 3, 4 and 5 by the following formula II

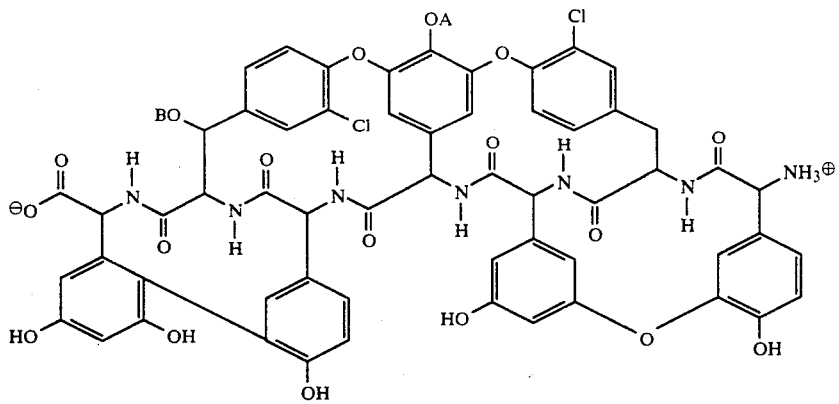

wherein A represents -N[(C$_{10}$-C$_{11}$)aliphatic acyl]-β-D-2-deoxy-2-aminoglucopyranosyl, B represent N-acetyl-β-D-2-deoxy-2-amino-glucopyranosyl, M represents -D-mannopyranosyl. More particularly in teicoplanin A$_2$ component 1, the [(C$_{10}$-C$_{11}$)-aliphatic acyl] substituent represents Z-4-decenoyl, in teicoplanin A$_2$ component 2 represents 8-methyl-nonanoyl, in teicoplanin A$_2$ component 3 represents decanoyl, in teicoplanin A$_2$ component 4 represents 8-methyldecanoyl, in teicoplanin A2 component 5 represents 9-methyldecanoyl.

All the sugar moieties, when present, are linked to the teicoplanin nucleus through O-glycosidic bonds.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046 and are described in European Patent Application Publication No. 119575 and European Patent Application Publication No. 119574, respectively.

Preferred hydrolysis conditions for the production of antibiotic L 17054 are: 0.5 N hydrochloric acid at a temperature between 70° C. and 90° C. and for a time which is generally between 15 and 90 min.

Antibiotic L 17054 is represented by the above formula II wherein A represents hydrogen, B represents N-acetyl-D-2-deoxy-2-amino-glucopyranosyl, M represents α-D-manno-pyranosyl wherein the sugar moieties are linked to the peptidic nucleus through an O-glycosidic bond.

Preferred hydrolysis conditions for the preparation of antibiotic L 17046 are: 1-3 N hydrochloric acid, at a temperature between 50° and 90° C. and for a time which is generally between 30 and 60 min.

Antibiotic L 17046 is represented by the above formula II wherein A and M represent hydrogen atoms, and B is N-acetyl-β-D-2-deoxy-2-amino-glucopyranosyl wherein the sugar moiety is linked to the peptidic nucleus through an O-glycosidic bond.

The complete selective cleavage of all the sugar moieties of the teicoplanin compounds gives an aglycone molecule which is called antibiotic L 17392, or deglucoteicoplanin, and is represented by the above formula II wherein A, B, and M each individually represents a hydrogen group. This selective hydrolysis process is described in European patent application No. 84114558.4.

A substance having the same structural formula is disclosed in European Patent Application Publication No. 0090578 and is named antibiotic A 41030 factor B.

This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

Some of the above named compounds, i.e. teicoplanin, teicoplanin A$_2$ complex, teicoplanin A$_2$ component 1, teicoplanin A$_2$ component 2, teicoplanin A$_2$ component 3, teicoplanin A$_2$ component 4, teicoplanin A$_2$ component 5, antibiotic L 17054, antibiotic L 17046, and any mixture thereof in any proportion, are suitable starting materials for the preparation of the derivatives of the invention.

In the present description and claims "teicoplanin starting material" is used to indicate any one of the above starting materials, i.e. teicoplanin as obtained according to U.S. Pat. No. 4,239,751, any further purification thereof, teicoplanin A$_2$ complex, a compound of formula II wherein A, represents hydrogen or -N[(C$_{10}$-C$_{11}$)aliphatic acyl]-β-D-2-deoxy-2-aminoglucopyranosyl wherein (C$_{10}$-C$_{11}$)aliphatic acyl has the above defined meanings, B represent hydrogen or N-acetyl-β-D-2-deoxy-2-amino-glucopyranosyl, M represents hydrogen or α-D-mannopyranosyl, with the proviso that A, B and M may not simultaneously represent hydrogen and M represent hydrogen only when A represent hydrogen, and a salt thereof, or a mixture thereof in any proportion.

The compounds of the invention are mainly obtained by treating the proper starting materials under controlled basic conditions which lead to the selective removal of N-acetyl-β-D-2-deoxy-2-glucosaminyl group from the teicoplanin starting molecule.

A basic treatment of teicoplanin or one of its factor, components, pseudoaglycons or aglycon has been described by Barna J. C. J. et al. in "Structure and conformation of epimers derived from the antibiotic teicoplanin" J. Antibiotics, 37: 1204–1208 (1984). The result of the basic treatment therein described however was that an epimerization in position 3 always occured leading to less active antimicrobial substances.

The basic conditions of the present process for preparing the compounds of the invention are such that the removal of the N-acetyl-β-D-2-deoxy-2-aminoglucopyranosyl group from the teicoplanin starting material takes place without simultaneously affecting the other sugar moieties. Since all the sugar moieties in the teicoplanin starting material, when present, are linked through glycosidic bonds to the peptide "core" of the molecule selective conditions are required to remove only one sugar moiety (namely the N-acetyl-D-2-deoxy-2-amino glucopyranosyl moiety). In addition, these selective conditions must be such that no epimerization, or a very low rate of epimerization occurs at any chiral centers of the molecule.

It has been found that suitable controlled basic conditions for preparing the compounds of the invention from the proper teicoplanin starting material include reacting the starting material in a polar organic solvent in the presence of a strong alkali at a temperature lower than about 60° C.

Representative examples of polar organic solvents are lower alkanols, lower alkyl carboxamides, lower alkyl sulfoxamides, lower alkyl phosphoramides, lower alkyl sulfoxides and lower alkyl sulfones and the like and mixtures thereof.

Lower alkanols as above described are alkanols of 1 to 4 carbon atoms including methanol, ethanol, propanol, 1-methylethanol, butanol and 2-methylpropanol.

The term "lower alkyl" as used above represents alkyl groups of 1, 2, 3 or 4 carbon atoms. Examples of lower alkyl carboxamides are dimethylformamide, diethylformamide and the like. A preferred lower alkyl sulfoxide is dimethyl sulfoxide, a preferred lower alkyl sulfone is dimethyl sulfone and a preferred lower alkyl phosphoramide is hexamethyl phosphoramide. According to a preferred embodiment of the process of the invention, the polar organic solvent as above defined is a mixture of a polar aprotic organic solvent and a polar protic organic solvent. Among those solvents defined above, preferred polar aprotic-solvents are tertiary alkyl amides, and dialkyl sulfoxides and sulfones, while preferred polar protic organic solvents are lower alkanols.

The basic conditions required for the displacement of the N-acetyl-D-2-deoxy-2-amino-glucopyranosyl group from the starting material are obtained by means of strong alkali. Preferred examples of said strong alkali are concentrated aqueous alkali metal hydroxides, alkali metal oxides and alkali metal alkoxides of 1, 2, 3 or 4 carbon atoms. The alkali metals are preferably sodium or potassium, and the preferred alkoxy groups are methoxy, ethoxy, propoxy, and butoxy.

When the base is represented by an alkali metal alkoxide the polar organic solvent is preferably the corresponding alkanol possibly in a mixture with polar aprotic solvents as above defined. For efficently performing the process of the invention the reaction environment must contain a limited amount of water. In general, it is already present in the starting materials which in many instances are hydrates.

When the strong alkali is an alkali hydroxide or oxide, an amount of water of about from 0.5 to 2% (w/w), or a 15-20 molar excess, is highly preferred. Higher amounts of water, negatively interfere with the reaction course by favouring side-reactions.

Also the reaction temperature needs to be controlled, and in general it should be kept below 60° C. Preferably the reaction temperature is between 0° C. and 50° C., and most preferably and conveniently is room temperature. The reaction time varies depending on the other reaction parameters. Since the reaction course may be followed by TLC or preferably HPLC procedures, the skilled man is capable of controlling the reaction conditions and deciding when the reaction is to be considered as completed.

A preferred embodiment of process of the invention is represented by a process as above described wherein the polar organic solvent is a mixture of dimethylformamide and dimethylsulfoxide, the strong alkali is aqueous concentrated sodium or potassium hydroxide and the reaction temperature is room temperature. Preferably, the proportion between dimethylformamide (DMF) and dimethylsulfoxide (DMSO) is from 4:1 to 3:2 (v/v), while the preferred concentration of the aqueous sodium or potassium hydroxide is between 85 and 90% (w/w). Another preferred embodiment of the process of the invention is represented by a process as above described wherein the strong alkali is an alkali metal alkoxide as above described and the polar organic solvent is the alkanol corresponding to said alkoxide optionally in the presence of a polar aprotic solvent as defined above which is preferably dimethylformamide. The preferred mixture strong alkali/polar organic solvent is in this case 1-10% methanolic sodium methoxide in dimethylformamide.

When the starting material is teicoplanin $A_2$ the corresponding compound without the N-acetyl-D-2-deoxy-2-aminoglucopyranosyl group in position 34 (see formula I) and with a C-N double bond (x = nil, y = additional bond) in position 35, 52 is obtained which is identified as compound I in Table I, below. Likewise, when a teicoplanin component is used as the starting material the corresponding de-glycosilated derivative with a C-N double bond in position 35, 52 is obtained.

When the starting material is antibiotic L 17054 the corresponding deglycosylated compound is obtained with a C-N double bond in position 35, 52. This is identified as compound II in Table I.

NMR analysis also in comparison with known structures shows that no major changes in the configuration of the whole molecule has occured in these two new compounds relatively to the starting materials i.e. starting from a compound of the above formula II wherein M represents D-mannopyranosyl and the other substituents are as above defined, the corresponding compound wherein x represent nil and y represents an additional bond is obtained by treatment under strong alkali conditions.

When the starting material is antibiotic L 17046, i.e. a starting material of the above formula II wherein A and M represent hydrogen atoms and the other substituents are as above defined, the corresponding deglycosylated compound is obtained with a C-C double bond in position 34, 35. In this case, depending on the basic condition employed, compound IV or compound V are obtained. More particularly, compound IV is obtained by treating antibiotic L 17046 under the basic conditions as described above either for a prolonged time or under the most drastic conditions. Compound V is, conversely, obtained under milder conditions such as for instance alkali metal alkoxide in a molar excess (50-100 times excess) in the presence of the corresponding alkanol at room temperature for about 24-72 h. Reaction for longer times affords compound IV as the product of the complete transformation of compound V. Compound IV may also be transformed under mild acid conditions into compound III, i.e. the compound of formula I wherein A and M represent hydrogen, x represents nil and y represents a double bond (see Table I).

A representative example of the mild acid conditions for the transformation of compound V into compound III is presented by an aqueous solution of a mineral acid, typically 0.5-1N hydrochloric acid. Compound I or compound II may also be transformed into compound III by strong acid hydrolysis in the presence of a solvent selected from ethers, ketones, and mixture thereof, which are liquid at room temperature. The term "ethers" includes cyclic ethers and di-ethers. According to a preferred embodiment the term "ethers" is identified through the following general formulas $$R\!-\!O\!-\!R_1 \text{ and } R_2O\!-\!(CH_2)_n\!-\!OR_3$$

where R and $R_1$ may be each independently selected from alkyl of 1 to 8 carbon atoms, cycloalkyl of 5 to 8 carbon atoms, phenyl and phenyl($C_1$-$C_4$)alkyl or taken together with the oxygen atom form a fully hydrogenated heterocyclic ring of 5 to 10 members; n is the integer 2 or 3 and R2 and R3 are each independently selected from lower alkyl of 1 to 4 carbon atoms, phenyl and phenyl-($C_1$-$C_4$)alkyl or taken together with the group $-O-(CH_2)_n-O-$ form a fully hydrogenated 5 to 10 heterocyclic ring. The term "ketones" refers to aliphatic ketones of 3 to 8 carbon atoms and includes cycloaliphatic ketones of 5 to 8 carbon atoms. Preferably, the "ketones" are identified by the following formula $$R_4\!-\!CO\!-\!R_5$$

wherein $R_4$ and $R_5$ are each independently selected from lower alkyl of 1 to 6 carbon atoms, with the proviso that the total number of carbon atoms in the above formula can never be higher than 8, or $R_4$ and $R_5$ taken together form a polymethylene chain of 4 to 7 carbon atoms. Among the solvents listed above the following are particularly preferred for the use in this acid hydrolysis reaction: tetrahydrofuran, tetrahydropyran, 1,2-dimethoxyethane, 1,2-diethoxyethane, dioxane and mixtures thereof. The solvent is usually employed in a large excess in comparison with the starting teicoplanin compound. Although the most suitable amount of solvent can be determined in each case depending on the specific solvent, solvent power and boiling point, in general it is preferred to carry out the acid hydrolysis in the presence of an amount of organic solvent corresponding to 10 to 50 milliliters of solvent per each gram of starting teicoplanin compound.

The strong acid necessary to carry out the hydrolysis reaction is selected from strong mineral acids and strong organic acids. Among the strong mineral acids hydrogen chloride, hydrogen bromide, concentrated sulfuric acid and concentrated phosphoric acid are preferred. Among the strong organic acids the alphahalogenated lower aliphatic acids, the alkanesulfonic acids, the polyfluoroalkanesulfonic acids, the cycloalkanesulfonic acids and the arylsulfonic acids are preferred with the following being the most preferred ones: trifluoroacetic acid, trichloroacetic acid, methanesulfonic acid, ethanesulfonic acid, trifluoromethanesulfonic acid and p-toluenesulfonic acid. In particular, 95% to 98% (w/w) sulfuric acid and 85% to 98% (w/w) ortofosforic acid, yield satisfactory results. Among the organic acids, 98% (w/w) methanesulfonic acid and 98% (w/w) trifluoroacetic acid are preferably employed.

Compound I may also be transformed into compound II by means of a controlled acid hydrolysis with a strong organic acid such as 75-95% aqueous trifluoroacetic acid at a temperature between 10° and 50° C. A preferred acid is 90% trifluoroacetic acid and the reaction temperature is preferably room temperature.

Although in the description and claims the term "solvent" is employed, according to the process of this invention it is not necessary that either the starting teicoplanin compound and/or the final antibiotic product of formula I be completely dissolved into the reaction solvent to form a homogeneous phase reaction solution. It is however necessary that the starting teicoplanin compound at the reaction temperature be sufficiently dissolved into the polar organic solvent/strong alkali mixture amount, that is, the concentration of the starting teicoplanin compound in the solution must not be so low that the reaction rate is very slow and/or a huge amount of solvent is required to perform the reaction on a pilot or industrial scale.

Table I below lists some representative compounds of the invention.

TABLE I

| Compound | A | M | x | y | 36,37-Bond |
|---|---|---|---|---|---|
| I | —GNHCOR | -M | nil | additional bond | trans |
| II | H | -M | nil | additional bond | trans |
| III | H | H | nil | additional bond | trans |
| IV | H | H | additional bond | nil | cis |
| V | H | H | additional bond | nil | trans |

—GNHCOR represents N[($C_{10}$-$C_{11}$)aliphatic acyl] β-D-2-deoxy-2-aminoglycopyranosyl as above defined for the teicoplanin $A_2$ components
-M represents α-D-mannopyranosyl The following table (Table II) lists the analytical results, salt form, (M+H)+ peak in the fast atom bombardment (FAB) mass spectra, and potentiometric and HPLC analysis results.

Analytical results for C, H, N, Cl were within ±0.4% of the theoretical values. The weight loss (solvent content), determined by thermogravimetric analysis (TGA), was always about 6-7%. The inorganic residue, determined in oxygen atmosphere at 900°, was always <0.3%. The analytical results refer to the salt form reported in the table.

FAB-MS positive ion spectra were recorded on a Kratos MS-50 instrument fitted with a standard FAB source and high field magnet. The sample was dispersed in a mixture thioglycerol:diglycerol 1:1 (v/v) and bombarded with a 6-9 KeV beam of Xe atoms.

Acid-base titration were carried out in 2-methoxyethanol METHYL CELLOSOLVE ® water 4:1 (v/v) solution, with 0.01 NaOH after addition of suitable amounts of 0.01N HCl. The equivalent weights (EW) given are corrected for the solvent content and the inorganic residue.

HPLC was run with a Varian Mod. 5000 LC pump equipped with a 20 μl injector Rheodyne Mod. 7125 and a UV detector at 254 nm.

Columns: a pre-column (5 cm) packed with perisorb RP-8 (30 μm) (Merck Co.) followed by a column hiber RT 250-4 (Merck Co.) (25 cm) pre-packed with LICHROSORB RP-8 (10 μm). *Chromatographic conditions:* eluent A, 0.2% aq. $HCO_2NH_4$; eluent B, 100% $CH_3CN$; linear gradient from 15 to 35% of B in A in 30 min at the flow rate of 2 ml/min; injection 20 μl. The reactions were monitored by injecting samples of the solutions diluted enough to obtain a final concentration of about 1 mg/ml.

Final products were checked by injecting solutions (20 μl) of 10 mg of each product in 10 ml of a mixture $CH_3CN:0.2\%$ aq. $HCO_2NH_4$ (or 0.1N HCl for compound III) 1:1 (v/v).

TABLE II

Physico-chemical and analytical data of representative compounds of the invention.

| COMPOUND | FORMULA (MW) | SALT FORM | FAB-MS (M + H) | *POTENTIOMETRIC $pK_{mcs}$ (EW) | HPLC ($t_R$, min) |
|---|---|---|---|---|---|
| I | — | HCl | n.d. | 5.0 (COOH) 6.9 ($NH_2$) (1870) | (component 1) 15.7 (component 2) 17.5 (component 3) 18.1 (component 4) 20.4 (component 5) 21.2 |
| II | $C_{64}H_{53}Cl_2N_7O_{22}$ (1343) | HCl | 1342 | 4.8 (COOH) 6.9 ($NH_2$) (1440) | 7.74 |
| III | $C_{58}H_{43}Cl_2N_7O_{22}$ (1181) | HCl | 1180 | n.d. | 10.06 |
| IV | $C_{58}H_{43}Cl_2N_7O_{22}$ (1181) | (internal salt) | 1180 | 4.8 (COOH) 7.1 ($NH_2$) (1300) | 11.18 |
| V | $C_{58}H_{43}Cl_2N_7O_{22}$ (1181) | (internal salt) | 1180 | n.d. | 12.24 |

*The data for teicoplanin $A_2$ were: $pK_{mcs}$ 5.0 (COOH), 7.1 ($HN_2$) with an average EW 1930;
The data for deglucoteicoplanin were: $pK_{mcs}$ 4.9 (COOH), 6.9 ($NH_2$) with EW 1407.
n.d. - Not determined.

TABLE III

Some significant $^1$H-NMR assignments for the compound I to V in comparison with deglucoteicoplanin (δ = ppm; m - multiplicity) $^1$H-NMR spectra were recorded in DMSO-$d_6$ at 30° C. with a Bruker WH-270 cryospectrometer, using tetramethylsilane (TMS) as the internal reference (δ = 0.00 ppm).

| PROTONS | I | (m) | II | (m) | III | (m) | IV | (m) | V | (m) | DEGLUCO-TEICOPLANIN |
|---|---|---|---|---|---|---|---|---|---|---|---|
| $C_{15}$—H | 4.69 | (s) | 4.66 | (s) | 4.67 | (s) | 4.67 | (s) | 4.56 | (s) | 4.62 (s) |
| $C_{18}$—H | 4.93 | (ddd) | 4.94 | (ddd) | 4.93 | (ddd) | 4.90 | (ddd) | 4.91 | (d) | 4.97 (d) |
| $C_3$—H | 5.33 | (d) | 5.29 | (d) | 5.28 | (d) | 5.69 | (d) | 5.29 | (d) | 5.34 (d) |
| $C_{50a}$—H | 5.67 | (d) | 5.65 | (d) | 5.55 | (d) | 5.67 | (d) | 5.56 | (d) | 5.67 (d) |
| $C_{48}$—H | 4.53 | (d) | 4.57 | (d) | 4.58 | (d) | 5.57 | (d) | 5.34 | (d) | 4.34 (d) |
| $C_{35}$—H | — | | — | | — | | — | | — | | 4.12 (dd) |
| $C_{38}$—H | 4.13 | (d) | 4.15 | (d) | 4.00 | (d) | 5.04 | (d) | 4.90 | (d) | 4.39 (d) |
| $C_{19}$—H | 2.86 | (dd) | 2.86 | (dd) | 2.82 | (dd) | 2.84 | (dd) | 2.88 | (dd) | 2.85 (dd) |
| $C_{34}$—H | 4.13 | (d) | 4.15 | (d) | 4.16 | (d) | * | (s) | * | (s) | 5.10 (d) |
| $C_{34}$—H | 4.76 | (d) | 4.83 | (d) | 4.93 | (d) | — | | — | | — |
| $C_{26}$—H | 5.59 | (s) | 5.58 | (s) | 5.40 | (s) | | | 5.57 | (s) | 5.51 (s) |
| $C_{27}$—H | 4.72 | (s) | 4.71 | (s) | 4.68 | (s) | | | 4.87 | (s) | 5.11 (s) |
| CH of MANNOSE | 3.48 | (m) | 3.48 | (m) | — | | — | | — | | — |
| ANOMERIC H of MANNOSE | 5.48 | (s) | 5.44 | (s) | — | | — | | — | | — |
| $N_{52}$—H | — | | — | | — | | 9.41 | (s) | 9.32 | (s) | 6.72 (d) |
| $N_{37}$—H | n.d. | | n.d. | | n.d. | | 6.76 | (d) | 7.54 | (d) | 8.36 (d) |

*Shifted in the aromatic region.
n.d. - not determined
m: s - singlet; d - doublet

TABLE IV

UV Spectral data $\lambda_{max}$, nm (ε) of the compounds I to V (UV spectra were run on a Unicam SP 800 Spectrophotometer).

| SOLVENT | COMPOUND | | | | |
|---|---|---|---|---|---|
| | I | II | III | IV | V |
| $CH_3OH$ | n.d. | n.d. | 282 | 278 | 280 |
| 0.1N HCl | 279 (26870) | 279 (18490) | 280 (23070) | 278 (14980) | 278 (15850) |
| 0.1N NaOH | 296 (17310) | 296 (17990) | 296 (16020) | 296 (18780) | 296 (23140) |
| $H_2O$ buffer pH 7.4 | 279 (24490) | 279 (25420) | 280 (22110) | n.d. | 278 (17650) |
| | (17650) | (19000) | | | (16540) | n.d. = not determined

TABLE V

IR Spectral data (ν, $cm^{-1}$) of the compounds I to V in comparison with deglucoteicoplanin (recorded on a Perkin Elmer 580 spectrometer in nujol mull).

| COMPOUND | NH, and PHENOLIC OH | AMIDE I | $\nu C{=}O$ (COO$\overline{H}$) (or COO) | δ $NH_3^+$ | AMIDE II | PHENOLIC δ OH and $\nu C{-}O$ | BENDING VIBRATION OF MANNOSE |
|---|---|---|---|---|---|---|---|
| I | 3280 (broad) | 1645 | 1610 | 1590 | 1510 | 1230, 1060, 1025-1010 | 970 |
| II | 3240 | 1650 | 1725 | 1590 | 1515 | 1225, 1060 | 970 |

TABLE V-continued

IR Spectral data ($v$, cm$^{-1}$) of the compounds I to V in comparison with deglucoteicoplanin (recorded on a Perkin Elmer 580 spectrometer in nujol mull).

| COMPOUND | NH, and PHENOLIC OH | AMIDE I | $vC=O$ (COO$\bar{H}$) (or COO) | $\delta$ NH$_3^+$ | AMIDE II | PHENOLIC $\delta$ OH and $vC-O$ | BENDING VIBRATION OF MANNOSE |
|---|---|---|---|---|---|---|---|
| III | (broad) 3300 (broad) | 1655 | (COOH) 1615 | 1590 | 1515 | 1005 1230, 1060 1010 | — |
| IV | 3400, 3280 (broad) | 1650 | 1615 | 1590 | 1520 | 1230, 1200, 1160, 1060 1020, 1005 | — |
| V | 3250 | 1650 | 1610 | 1590 | 1510 | 1230, 1200 1135, 1060, 1005 | — |
| DEGLUCO-TEICOPLANIN | 3300 | 1655 | 1610 | 1590 | 1515 | 1230, 1140, 1060, 1005 | — |

The antibacterial activity of the compounds of the invention can be demonstrated in vitro by means of standard agar-dilution tests.

ISOSENSITEST broth (Oxoid) and TODD-HEWITT broth (Difco) are used for growing staphylococci and streptccocci, respectively. Broth cultures are diluted so that the final inoculum is about $10^4$ colony forming units/ml (CFU/ml). Minimal inhibitory concentration (MIC) is considered as the lowest concentration which shows no visible growth after 18-24 h incubation at 37° C. The results (MIC) of the antibacterial testing of representative compounds of formula I are summarized in the following Table VI:

TABLE VI

| ORGANISMS | | In vitro antimicrobial activity (MIC, $\mu$g/ml) COMPOUND | | | | |
|---|---|---|---|---|---|---|
| | | I | II | III | IV | V |
| S. aureus | ATCC 6538 | 0.5 | 0.25 | 0.25 | 1 | 2 |
| S. aureus | TOUR | 0.5 | 0.25 | 0.25 | 1 | 4 |
| S. epidermidis | ATCC 12228 | 0.25 | 0.5 | 0.12 | 0.12 | 0.4 |
| S. pyogenes | C 203 | 0.06 | 2 | 1 | 4 | 8 |
| S. pneumoniae | UC 41 | 0.06 | 2 | 1 | 4 | 8 |
| S. faecalis | ATCC 7080 | 1 | 1 | 1 | 8 | 16 |
| E. Coli | SKF 12140 | >128 | >128 | >128 | >128 | >128 |
| P. vulgaris | ATCC 881 | >128 | >128 | >128 | 128 | >128 |

In a representative experiment, compound III i.e. (35,52-di-dehydro-34-deoxy-teicoplanin aglycon) was tested against some clinically isolated coagulase-negative staphylococci. The results of the test, in comparison with teicoplanin, are reported below in Table VII. The MIC were determined in microtiter using ISO-SENSITEST broth (Oxoid Co.) and approximately $10^4$ CFU/ml as the inoculum.

TABLE VII

In vitro activity against coagulase-negative staphylococci, clinical isolates.

| ORGANISM | MIC (mcg/ml) | |
|---|---|---|
| | COMPOUND (III) | TEICOPLANIN |
| S. epidermidis L 1378 | 0.125 | 0.5 |
| S. simulans* L 785 | 0.125 | 0.25 |
| S. Simulans* L 1142 | 0.125 | 0.125 |
| S. hominis L 1070 | 0.125 | 0.25 |
| S. warneri L 1375 | 1 | 2 |
| S. haemoliticus* L 1520 | 0.5 | 4 |

*Methicillin-resistant

In addition to their antibacterial activity in vitro, the compounds of the invention shown also antibacterial activity in in vivo experiments. In particular, in an experimental infection in mice conducted as described by V. Arioli et al., Journal of Antibiotics 29, 511 (1976) compounds I, II, and III showed an ED$_{50}$ value of 0.35, 5.8 and 5 mg/Kg, respectively. In view of the above reported antimicrobial activity, the compounds of the present invention can effectively be employed as the active ingredients of antimicrobial preparations used in human and veterinary medicine for the prevention and treatment of infectious diseases caused by pathogenic bacteria which are susceptible to said active ingredients.

In such treatments, these compounds may be employed as such or in the form of mixtures in any proportion.

The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compound of the invention are generally effective at a dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit.

Representative examples of preparation of pharmaceutical compositions are as follows:

A parenteral solution is prepared with 100 mg of compound I dissolved in 2 ml of sterile water for injection. A parenteral solution is prepared with 250 mg of compound II dissolved in 3 ml of sterile water for injection.

A topical ointment is prepared with 200 mg of compound III 3.6 g of polyethylene glycol 400 U.S.P.
6.2 g of polyethylene glycol 4000 U.S.P.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Ore., USA, 1977) and are incorporated herein by reference.

The following examples further illustrate the invention.

EXAMPLE 1 a) Preparation of
42-α-D-mannosyl-56-N-acyl-β-D-glucosaminyl-35,52-didehydro-34-deoxy-teicoplanin aglycon (Compound I)

A solution of 50 g (0.75 mol) of commercial 85% KOH in 1 liter of $CH_3OH$ is added dropwise at room temperature to a stirred solution of 23 g (12 mmol) of teicoplanin (containing about 15% w/w of water) in 2.5 l of mixture DMF/DMSO 3:2 (v/v). The resulting suspension is stirred at room temperature (the reaction vessel being sealed with a valve containing soda lime) for 24 h. After standing 48 h at 10° C., 1 liter of methanol is added and the resulting brown solution is stirred at room temperature for 2 h. By adding 1 liter of ether a solid separates which is collected and suspended in 1 liter of methanol. The insoluble is collected, washed with 1 liter of ether and dried in vacuum at room temperature overnight over $P_2O_5$, yielding 21 g of the crude compound of the title in the form of the corresponding potassium salt.

7 g of this crude potassium salt is dissolved in 400 ml of a mixture $CH_3CN/H_2O$ 1:2 (v/v) and the resulting cloudy solution is brought to pH 2.8 with glacial acetic acid, then 25 g of silanized silica gel SILICOGEL 60, Merck Co.; 0.06–0.2 mm) and 500 ml of butanol are added. The solvents are completely evaporated under reduced pressure and the residue is placed on top of a column containing 1.5 Kg of the same silanized silica gel in 0.01M aqueous $NH_4H_2PO_4$. The column is developed with a linear gradient from 10% to 70% $CH_3CN$ in 0.5% aq. acetic acid in 30 h at a rate of 300 ml/h. Fractions of 25 ml each are collected and checked by HPLC. Those containing the five pure components of the complex of the title are pooled, butanol is added and the mixture is concentrated until both $CH_3CN$ and $H_2O$ are completely removed. Then 5 ml of 1N HCl is added and the solution is concentrated to a small volume. Ethyl acetate is then added to precipitate a solid which is collected by filtration, washed with ether and dried in vacuo at room temperature overnight, yielding 5.04 g of pure hydrochloride of the compound of the title.

b) Preparation of the internal salt

A solution of 1.7 g (1 mmol) of this hydrochloride in 200 ml of a mixture of $H_2O/CH_3CN$ 2:1 (v/v) is adjusted to pH 6 with 0.1N NaOH. After adding 80 ml of butanol, the mixture is concentrated to a final volume of about 40 ml. A solid separates which is collected by filtration washed, subsequently with 50 ml of water and a mixture of acetone/ethyl ether 1:2 (v/v) and dried in vacuum at room temperature (over $P_2O_5$) for 48 h, yielding 1.4 g of the title compound, as the internal salt.

EXAMPLE 2

Preparation of
42-α-D-mannosyl-35,52-didehydro-34-deoxy-teicoplanin aglycon. (Compound II)

a) From Antibiotic L 17054

A solution of 1.8 g (27 mmol) of commercial 85% KOH in 200 ml of methanol is added at room temperature to a stirred solution of 1.1 g (0.7 mmol) of antibiotic L 17054 in 300 ml of a mixture DMF/DMSO 3:2 (v/v). The suspension which forms is stirred at room temperature for 30 h then 800 ml of ethyl ether is added. The precipitate is collected, washed with ether and dried in vacuo at room temperature overnight, yielding 1.2 g of crude compound of the title as the potassium salt, which is then purified by column chromatography on a column packed with 750 g of silanized silica gel under the conditions described above for compound I, but eluting with a linear gradient from 5% to 35% acetonitrile in water in 24 h at a rate of 250 ml/h. Fractions containing the pure compound of the title are pooled and worked up as described in the foregoing example. After removing both acetonitrile and water, 1 ml of 1N HCl is added to the resulting butanolic solution which is concentrated to a final volume of about 40 ml. By adding ether a solid separates which is collected, by filtration washed with ether and dried in vacuo overnight at 35° C., yielding 0.6 g of the hydrochloride of the compound of the title.

b) From compound I i) A solution of 5 g (3 mmol) of compound I as obtained by following the procedure of the foregoing example 1 in 60 ml of 90% aqueous trifluoroacetic acid (TFA) is stirred for 10 min at 5° C. and 90 min at room temperature. Then 240 ml of ethyl ether is added and the precipitate which separates is collected and redissolved in 200 ml of methanol. The insoluble is removed by filtration and the filtrate is concentrated to a small volume under reduced pressure. By adding ether, a solid separates which is collected, washed with ether and dried in vacuo at 35° C. overnight, yielding 3.96 g of pure trifluoroacetate of the compound of the title.

ii) A solution of 6 g (3 mmol) of crude (85% titre by HPLC expressed as the percentage of the areas of peaks; the impurities were due to undefined by-products) compound I potassium salt in 100 ml of 90% aqueous TFA is stirred 15 min at 0° C. and 2 h at room temperature. The solvents are completely evaporated at room temperature under reduced pressure. The oily residue is dissolved in 150 ml of a mixture of $H_2O:CH_3CN$ 1:1 (v/v) and the resulting solution is diluted with 300 ml of water and loaded at the top of a column containing 750 g of silanized silica gel in the mixture 0.5% aq. $HCO_2NH_4$ $CH_3CN$ 90:10 (v/v). The column is first washed with 500 ml of the mixture $H_2O:CH_3CN$ 85:15 (v/v) and then developed with a linear gradient from 15 to 30% of acetonitrile in 0.001N HCl in 24 h at the rate of 250 ml/h, while collecting 25 ml fractions. Those containing the pure compound of the title were pooled. Some crystalline product present is collected, washed with a mixture acetonitrile/ethyl ether 1:2 (v/v) and dried in vacuum at room temperature overnight (over $P_2O_5$), yielding 0.85 g of pure compound of the title, as the internal salt. The mother liquors are concentrated after adding enough butanol to obtain a final dry butanolic suspension of about 200 ml. After adding 3 ml of 1N HCl, a clear solution forms which is concentrated to a small volume under reduced pressure. By adding ethyl ether, a solid separates which is collected by filtration, washed with ether and dried in vacuo at room temperature overnight (over KOH pellets), obtaining 2.3 g of pure hydrochloride of the compound of the title.

EXAMPLE 3

Preparation of 35,52-didehydro-34-deoxy-teicoplanin aglycon. (Compound III)

a) From compound I

Dry HCl is slowly bubbled into a stirred suspension of 0.6 g of Compound I (see example 1 for its preparation) in 50 ml of dimethoxyethane (DME), while maintaining the internal temperature at 15°–20° C. A clear solution forms in a few hours which is then evaporated to dryness under reduced pressure. The residue is dissolved in 100 ml of a mixture $H_2O:CH_3CN$ 75:25 (v/v) and the resulting solution is loaded at the top of a column of 100 g of silanized silica gel in $H_2O$. The column is developed with a linear gradient from 25 to 60% $CH_3CN$ in 0.001N HCl in 20 h at the rate of 150 ml/h, while collecting 15 ml fractions. Those containing pure compound III are pooled and concentrated after adding enough butanol to obtain a final dry butanolic solution of about 100 ml. By adding 300 ml of dry hydrochloric ethyl ether, a solid separates which is collected, washed with ether and dried in vacuo at room temperature for 48 h (over KOH pellets), obtaining 0.35 g of the title compound, as the hydrochloride.

b) From compound II

To a stirred suspension of 3 g of Compound II (see example 2 for its preparation) in 100 ml of dimethoxyethane (DME) 25 ml of 96–98% $H_2SO_4$ is added dropwise while cooling to 0° C. The solution which forms is stirred at room temperature for 5 h, then 250 ml of ether is added and the solid which separates is collected, washed with ether and dried in vacuo at room temperature overnight, yielding 2.5 g of the title compound, as the sulfate.

c) From Compound V

Pure Compound V (50 mg) as obtained according to the procedure of example 5, below, is dissolved in 100 ml of 1N HCl at room temperature. After 5 h of reaction, a mixture 5:95 of Compound V and compound III is obtained. Compound III is then separated from the mixture by column chromatography on silanized silicagel, according to the procedure described above (a).

EXAMPLE 4

Preparation of (36,37-cis-51,52-trans)-34,35-didehydro-34-deoxy-teicoplanin-aglycon. (Compound IV)

a) From antibiotic L 17046

A solution of 7.5 g (0.12 mol) of commercial 85% aqueous KOH in 200 ml of $CH_3OH$ was added at room temperature to a stirred solution of 5 g (~3.5 mmol) of antibiotic L 17046 in 200 ml of DMF (soda lime valve). After 20 h, 10 ml of acetic acid is added dropwise at 5°–10° C. and the solution is poured into 1.5 l of ethyl ether. The precipitate which separates is collected by filtration and redissolved in 3 l of a mixture $H_2O/n$-$C_4H_9OH/CH_3OH$ 3:2:1 (v/v/v) with vigorous stirring while adjusting the pH to 3.5 with glacial acetic acid. The organic layer is separated, washed with 1 l of $H_2O$, then concentrated to a final volume of about 200 ml. By adding 250 ml of ether, a solid separates which is collected, washed with ether and dried in vacuo at room temperature overnight, yielding 1.7 g of pure compound of the title.

b) From Compound III or Compound V

The compound of the title (Compound IV (36,37-cis-51,52-trans)-34,35-didehydro-34-deoxy-teicoplaninaglycon) is also obtained from compound III (see example 3 for its preparation) or compound V (see example 5 for its preparation) with the same yields substantially according to the procedure described in the above example 4 a) in the case of antibiotic L 17046 as the starting material

EXAMPLE 5

Preparation of (36,37-trans-51,52-trans)-34,35-didehydro-34-deoxy-teicoplanin-aglycon. (Compound V)

a) From antibiotic L 17046

A solution of 6 g (0.11 mol) of freshly prepared $NaOCH_3$ in 300 ml of $CH_3OH$ is added at room temperature to a stirred solution of 2.8 g (2 mmol) of antibiotic L 17046 in 300 ml of a mixture DMF/DMSO 4:1 (v/v).

The resulting solution is stirred at room temperature for 72 h in a vessel sealed with a soda lime valve. After cooling to 0°C., 7 ml of glacial acetic acid is added dropwise while maintaining the temperature at 0-10° C. Methanol is removed by evaporation at 30° C. under vacuum and the precipitate which separates is filtered off and discarded. The filtrate is poured into 1.5 l of water and the pH of the resulting cloudy solution is adjusted to 6 with glacial acetic acid. The mixture is extracted with 2 l of n-$C_4H_9OH/CH_3CO_2C_2H_5$ 3:1 (v/v). The organic layer is separated and concentrated to a small volume under reduced pressure. By adding ethyl ether, a solid separates which is collected, washed with ether and dried in vacuo at room temperature overnight, yielding 0.95 g of crude compound of the title which is dissolved in 100 ml of a mixture of $CH_3CN/H_2O$ 1:1 (v/v). The suspension obtained after adding 5 g of silanized silica gel (SILICAGEL 60; Merck Co.; 0.06-0.2 mm) and 200 ml of water is stirred at room temperature for 30 min and put at the top of a column containing 200 g of the same silanized silica gel in water. This column is initially developed with 200 ml of a 0.01M solution of aqueous $HCO_2NH_4$, then with a linear gradient from 2 to 40% $CH_3CN$ in $H_2O$ in 20 h at a rate of 200 ml/h. Fractions of 20 ml each were collected and checked by HPLC. Those containing pure Compound V are pooled, butanol is added and the mixture is concentrated until both acetonitrile and water are completely removed. By adding ether a precipitate separates which is collected, washed with ether and dried in vacuum at room temperature overnight, yielding 0.22 g of pure compound of the title.

b) From Compound III

One gram of compound III is dissolved in 2 liters of a mixture $CH_3CN:H_2O$ 1:1 (v/v), then 2 g of $NaHCO_3$ is added at room temperature. The solution is shaken for 30 sec and left standing at room temperature while monitoring the course of the reaction by HPLC (injections of 10 μl each).

After 30 and 50 min, a 58% and 90% transformation of Compound III into Compound V is observed.

The identity of Compound V is confirmed by comparison with an authentic sample. The recovery of compound III is carried out as described above (a), i.e. acidification to pH 6 with glacial acetic acid, evaporation of the organic solvent, extraction with n—$C_4H_9OH/CH_3CO_2C_2H_5$ 3:1 (v/v), isolation of the crude powder and purification by reverse phase column chromatography.

We claim:

1. A process for preparing a compound of formula I

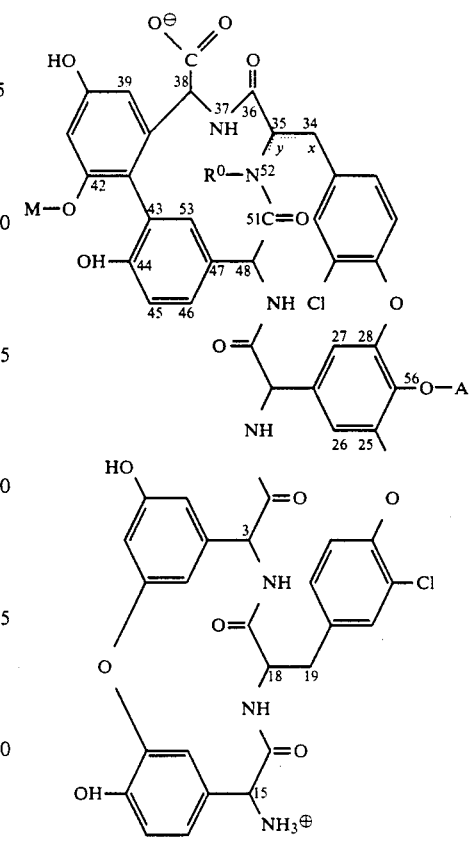

wherein the Chiral centers of this moiety have the same configuration as the starting materials of formula II reported below, x and y each represents nil or an additional bond, A represents hydrogen or N[($C_{10}$-$C_{11}$) aliphatic acyl]-β- D-2-deoxy-2-aminoglucopyranosyl, M represents hydrogen or α-D-mannopyranosyl, $R^0$ represents nil when y represents an additional bond, and hydrogen when y represents nil, with the proviso that when x represents an additional bond y must represent nil, and when x represents nil y must represent an additional bond and that when M represents hydrogen also A must represent hydrogen, or an addition salt thereof, which comprises treating a teicoplanin starting material of formula II,

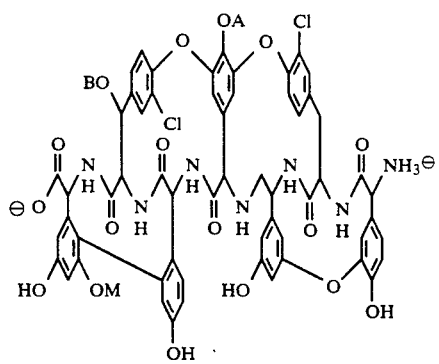

wherein A represents hydrogen or —N[($C_{10}$-$C_{11}$) aliphatic acyl]-β-D-2-deoxy-2 -amino-glucopyranosyl wherein B represents N-acetyl-β-D-2-deoxy-2-aminoglycopyranosyl, M represents hydrogen or α-D-mannopyranosyl, with the proviso that M represents hydrogen only when A represents hydrogen, or a salt thereof, or a mixture thereof in any proportion, in a polar organic solvent in the presence of a strong alkali selected from alkali metal hydroxides, oxides and alkoxides of 1, 2, 3, or 4 carbon atoms, at a temperature lower than about 60° C.

2. A process according to claim 1, wherein the polar solvent is selected from ($C_1$-$C_4$) alkanols, ($C_1$-$C_4$) alkyl carboxamides, ($C_1$-$C_4$) alkyl sulfoxamides, ($C_1$-$C_4$) alkyl phosphoramides, ($C_1$-$C_4$) alkyl sulfoxides and ($C_1$-$C_4$)-alkyl sulfones and mixtures thereof.

3. A process according to claim 1 wherein the polar solvent is selected from dimethylformamide, diethylformamide, dimethylsulfoxide, dimethylsulfone, hexamethylphosphoramide and mixtures thereof.

4. A process according to claim 1 wherein the reaction environment contains from 0.5 to 2% (w/w) of water.

5. A process according to claim 1 wherein the reaction environment contains from 15 to 20 times molar excess of water over the teicoplanin starting material.

6. A process according to claim 1 wherein the reaction temperature is between 0° and 50° C.

7. A process according to claim 1 wherein the reaction temperature is room temperature.

8. A process according to claim 1 wherein the polar organic solvent is a mixture of dimethylformamide, and dimethylsulfoxide the strong alkali is concentrated aqueous sodium or potassium hydroxide.

9. A process according to claim 8 wherein the proportion between dimethylformamide (DMF) and dimethylsulfoxide (DMSO) is between 4:1 to 3:2, v/v while the concentration of the aqueous sodium or potassium hydroxide is between 85 and 90% (w/w).

10. A process according to claim 1 wherein the strong alkali is an alkali metal alkoxide and the polar organic solvent is the alkanol corresponding to said alkoxide optionally in the presence of a polar aprotic solvent.

11. A process according to claim 1 wherein the strong alkali is sodium or potassium methoxide, and the polar organic solvent is a mixture methanol/dimethyl formamide.

* * * * *